United States Patent
Verschuren et al.

(10) Patent No.: US 8,411,274 B2
(45) Date of Patent: Apr. 2, 2013

(54) MICROELECTRONIC SENSOR DEVICE FOR OPTICAL EXAMINATIONS ON A WETTED SURFACE

(75) Inventors: Coen Adrianus Verschuren, Eindhoven (NL); Albert Hendrik Jan Immink, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 153 days.

(21) Appl. No.: 12/666,814

(22) PCT Filed: Jun. 24, 2008

(86) PCT No.: PCT/IB2008/052498
§ 371 (c)(1),
(2), (4) Date: Apr. 26, 2010

(87) PCT Pub. No.: WO2009/001289
PCT Pub. Date: Dec. 31, 2008

(65) Prior Publication Data
US 2010/0328654 A1 Dec. 30, 2010

(30) Foreign Application Priority Data
Jun. 28, 2007 (EP) ..................... 07111286

(51) Int. Cl.
*G01N 21/55* (2006.01)
*G01J 1/10* (2006.01)

(52) U.S. Cl. .................. 356/445; 356/243.1; 356/243.4
(58) Field of Classification Search ........... 356/445–448
See application file for complete search history.

(56) References Cited

U.S. PATENT DOCUMENTS

| 4,551,308 | A | 11/1985 | Mintz |
| 5,059,394 | A | 10/1991 | Phillips et al. |
| 5,067,092 | A | 11/1991 | Hamann |
| 5,084,620 | A | 1/1992 | Butturini |
| 5,114,350 | A | 5/1992 | Hewett |
| 5,508,521 | A | 4/1996 | Kraft et al. |
| 5,525,514 | A | 6/1996 | Jacobs et al. |
| 5,708,278 | A | 1/1998 | Lowne |
| 5,973,775 | A | 10/1999 | Blitzke |
| 6,024,919 | A | 2/2000 | Nelson et al. |
| 6,071,294 | A | 6/2000 | Simons et al. |
| 6,211,954 | B1 | 4/2001 | Danielzik et al. |
| 6,289,144 | B1 | 9/2001 | Neuschafer et al. |
| 6,448,067 | B1 | 9/2002 | Tajnafoi |
| 6,707,554 | B1 | 3/2004 | Miltner et al. |
| 6,736,957 | B1 | 5/2004 | Forrow et al. |

(Continued)

FOREIGN PATENT DOCUMENTS

| WO | 2004102183 A2 | 11/2004 |
| WO | 2004113886 A1 | 12/2004 |

(Continued)

*Primary Examiner* — Michael P Stafira

(57) ABSTRACT

A method and a microelectronic sensor device for making optical examinations in an investigation region at the contact surface of a carrier, wherein an input light beam is sent from a light source towards the investigation region, and wherein an output light beam coming from the investigation region is detected by a light detector. An evaluation unit that is coupled to the light detector is adapted to determine the wetting grade of the investigation region based on a characteristic parameter of the output light beam. The evaluation unit may be adapted to determine a change in the light intensity caused by a liquid contacting the contact surface. The wetting grade may be detected in a test region that is located adjacent to the investigation region and that has a higher roughness than the investigation region.

16 Claims, 3 Drawing Sheets

U.S. PATENT DOCUMENTS

| | | |
|---|---|---|
| 6,750,053 B1 | 6/2004 | Widrig Opalsky et al. |
| 6,887,429 B1 | 5/2005 | Marshall et al. |
| 7,015,046 B2 | 3/2006 | Wohlstadter et al. |
| 7,022,286 B2 | 4/2006 | Lemke et al. |
| 7,070,920 B2 | 7/2006 | Spivey et al. |
| 7,132,078 B2 | 11/2006 | Rawson et al. |
| 2002/0021443 A1 | 2/2002 | Venkatasubbarao et al. |
| 2004/0136871 A1 | 7/2004 | Pachl et al. |
| 2005/0048599 A1 | 3/2005 | Goldberg et al. |
| 2005/0088648 A1 | 4/2005 | Grace et al. |
| 2006/0163458 A1 | 7/2006 | Reime |
| 2006/0228259 A1 | 10/2006 | Samsoondar |
| 2007/0031283 A1 | 2/2007 | Davis et al. |

FOREIGN PATENT DOCUMENTS

| | | |
|---|---|---|
| WO | 2005124300 A1 | 12/2005 |
| WO | 2006038149 A1 | 4/2006 |
| WO | 2008072156 A2 | 6/2008 |

MICROELECTRONIC SENSOR DEVICE FOR OPTICAL EXAMINATIONS ON A WETTED SURFACE

The invention relates to a microelectronic sensor device and a method for optical examinations in an investigation region at the contact surface of a carrier, comprising the emission of light into the investigation region and the observation of light coming from the investigation region. Moreover, it relates to a carrier for and the use of such a device.

The US 2005/0048599 A1 discloses a method for the investigation of microorganisms that are tagged with particles such that a (e.g. magnetic) force can be exerted on them. In one embodiment of this method, a light beam is directed through a transparent material to a surface where it is totally internally reflected. Light of this beam that leaves the transparent material as an evanescent wave is scattered by microorganisms and/or other components at the surface and then detected by a photodetector or used to illuminate the microorganisms for visual observation. A problem of this and similar measurement principles is that they are very sensitive to disturbances and variations in the operating conditions that typically occur if a disposable carrier is manually exchanged and/or if a sample fluid is exchanged.

Based on this situation it was an object of the present invention to provide means for optical examinations in an investigation region that comprises for example a biological sample. In particular, it is desirable that these means are robust with respect to variations and disturbances introduced by the exchange of samples and/or sample carriers.

This object is achieved by a microelectronic sensor device according to claim 1, a carrier according to claim 13 and 14, respectively, a method according to claim 15, and a use according to claim 16. Preferred embodiments are disclosed in the dependent claims.

The microelectronic sensor device according to the present invention is intended for making optical examinations in an investigation region at the contact surface of a carrier (wherein the investigation region and the carrier do not necessarily belong to the device). In this context, the term "examination" is to be understood in a broad sense, comprising any kind of manipulation and/or interaction of light with some entity in the investigation region, for example with biological molecules to be detected. The investigation region will typically be a small volume at the contact surface of the (preferably transparent) carrier in which material of a sample to be examined can be provided. The term "contact surface" is chosen primarily as a unique reference to a particular part of the surface of the carrier, and though target components of a sample will in many applications actually come into contact and bind to said surface, this does not necessarily need to be the case. The microelectronic sensor device comprises the following components:

a) A light source for emitting a light beam, called "input light beam" in the following, towards the contact surface. The light source may for example be a laser or a light emitting diode (LED), optionally provided with some optics for shaping and directing the input light beam.

b) A light detector for determining a characteristic parameter of a light beam, wherein said beam comes from the contact surface and will be called "output light beam" in the following. This output light beam will usually comprise light that is related to the input light beam, for example fluorescence light stimulated by the input light beam or reflected input light, wherein this component often carries some information one is interested in. The light detector may comprise any suitable sensor unit or plurality of sensor units by which the characteristic parameter can be detected, for example a photodiode, a photo resistor, a photocell, or a photo multiplier tube.

c) An evaluation unit for detecting the wetting grade of the investigation region based on the determined characteristic parameter of the output light beam. The evaluation unit may be realized by dedicated analog electronic hardware, digital data processing hardware with associated software, and/or a mixture of both. The "wetting grade" reflects how much of the contact surface in the investigation region is actually contacted ("wetted") by a particular sample fluid and how much of it is not contacted ("un-wetted"). The medium that contacts the un-wetted parts of the investigation region may in principle be any solid material, liquid or gas different from the sample fluid, or the vacuum. In the practically relevant case that the medium is a gas, the wetting grade is an indication of the extent to which gas bubbles are attached to the contact surface. It may in the most simple case have just two values representing the states of "wetted" and "un-wetted" (dry). In general, the wetting grade will however have a plurality of values corresponding to different degrees of the wetting or even a continuum of values that may for example represent the wetted fraction of the contact surface (i.e. the percentage of a considered area which is contacted by sample fluid).

The described microelectronic sensor device has the advantage that it allows to take the wetting grade of the surface at which optical examinations take place into consideration. Thus the robustness and accuracy of the examinations can considerably be improved, because the wetting grade turns out to be a crucial operating condition. A reduced wetting degree due to e.g. gas bubbles at the contact surface can for example lead to a drastic underestimation of the concentration of target components one is interested in. Moreover, the sensor device has the advantage to derive the wetting grade optically from an output light beam. Most of the necessary hardware is therefore often already present in the setup of the underlying optical examination procedure.

There are many possibilities to define the "characteristic parameter" of the output light beam that is determined by the light detector. One practically important example of a characteristic parameter comprises the amount of light of the output light beam, wherein said amount is typically expressed as the (average) light intensity in a reference area. In many applications, the amount of light in the output light beam comprises information one is interested in, for example about the concentration of target components in the investigation region, and will therefore already be measured in the course of the optical examinations. The determination of the wetting grade can thus be achieved as a side effect.

In a particular embodiment of the invention, the evaluation unit is adapted to determine and compare the characteristic parameters measured before and after a fluid has been applied to the contact surface, respectively, wherein the application of the fluid may for example be the introduction of a sample liquid into an initially dry sample chamber or vice versa. The determination of the wetting grade can thus be based on a change in the measured characteristic parameter, which is usually less dependent of the particular measurement conditions than a determination from an absolute value only.

In another embodiment of the invention, which may preferably be combined with the aforementioned one, the evaluation unit is adapted to receive triggering signals from a fluid controller (e.g. a valve, pump or swab-squeezer) which controls the application of fluid to the contact surface. The fluid controller may be considered as a component of the microelectronic sensor device or an external, separate device; in the latter case, the protocol of the triggering signals should be well-defined to allow a safe communication of the evaluation unit with different types of such fluid controllers. With the help of the triggering signals, the evaluation unit can for example be alerted that the insertion of fluid into a sample chamber is going to take place or has taken place. This allows to compare measurement values of the characteristic parameter in definite states before, during and/or after the exchange of the medium adjacent to the contact surface. Furthermore, fluid detection allows the micro-electronic sensor device to start assay-device methods (e.g. magnetic actuation when performing magnetic label assays) at a predefined time. Additionally, it allows the micro-electronic sensor device to switch between different modes (e.g. a low power mode that only detects fluids and a high power mode that does full evaluation of the investigation region).

The evaluation unit may optionally be adapted to determine and compare the characteristic parameters before and after a carrier is placed into the reach of the input light beam. In this way, the evaluation unit can additionally be used to verify the correct placement of the carrier in the reader device, which helps to avoid errors due to e.g. manual handling mistakes.

In a further development of the invention, the light source comprises a beam regulator for at least temporarily emitting the input light beam into the surroundings of the investigation region. Thus the wetting grade in said surroundings can be detected, which can be assumed to be approximately the same as the wetting grade inside the investigation region itself. An advantage of such an indirect detection is that the carrier can be optimally designed for the optical examinations (in the investigation region) and for the detection of the wetting grade (in the surroundings), too. The surface of a glass carrier can for example be made smooth inside the investigation region, while it is rough in the surroundings for an improved detection of gas bubbles.

The microelectronic sensor device may optionally comprise a scanning unit for moving a single light beam, a switching unit for switching between at least two light beams, and/or a collimator unit for changing the width of the input light beam. All these designs allow the use of two or more different beams, wherein one of these beams may be optimal for the underlying optical examinations while the other is best suited for the detection of the wetting state. In particular, one of the beams may be a restricted input light beam that only reaches the investigation region, while the other beam is an input light beam like the one mentioned above that reaches the surroundings of the investigation region.

The light detector may optionally comprise a plurality of different sensor units that are associated to different components of the output light beam. In particular, the different sensor units may be associated to spatially different components of the output light beam, for example to central components that comprise only light coming from the investigation region or to peripheral components that comprise light coming from the surroundings of the investigation region. The optical examinations in the investigation region and the detection of the wetting grade in its surroundings can then be made simultaneously.

Preferably, the microelectronic sensor device comprises a signaling unit for (e.g. acoustically or optically) indicating the wetting grade of the investigation region to a user. The user can then take appropriate measures, for example an exchange of the carrier and/or of the sample fluid, to avoid examinations under wrong operating conditions.

In another embodiment, the microelectronic sensor device comprises a wetting regulator for adjusting the wetting grade of the investigation region. The wetting regulator may for example comprise an ultrasonic vibrator that can be used to remove gas bubbles from the contact surface in case of an insufficient wetting.

In a further development, the microelectronic sensor device comprises a high-level "operation controller" for controlling the light source, the light detector, means for magnetic actuation (e.g. an electromagnet), means for sample heating (e.g. an electrical resistor), means for dried-label agitation (e.g. ultrasonic probe) and/or optionally further components in dependence on the wetting grade determined by the evaluation unit. The operation controller can for example block optical examinations as long as the wetting grade is insufficient. Thus a timely start of assay-device procedures to control the biochemical assay is possible (e.g. magnetic actuation in case of a magnetic label assay). Furthermore, the microelectronic sensor device can be kept in a low-power-dissipation mode during wetting detection and can switch to a high-power-dissipation assay detection mode based on the signal extracted from the wetting detector.

According to a particular embodiment of the aforementioned design, the operation controller is adapted to initiate an optical examination in the investigation region after a predetermined wetting grade has been detected. Such an automatic start of the optical examinations has the advantage to provide better reproducible and comparable results, because variations of a manual start of the examinations can be avoided.

The invention further relates to a carrier for a microelectronic sensor device of the kind described above, wherein said carrier comprises a contact surface with an investigation region and wherein said contact surface has at least locally a roughness of more than about 30 nm, preferably more than about 100 nm. In this context, the "roughness" of a surface is quantitatively defined as the average roughness $R_a$, i.e. the average distance (measured perpendicular to the medium plane of the surface) a point on the surface has from the medium plane of the surface. The roughness should for the rough regions of the carrier differ significantly from "optically smooth", which typically corresponds to a value of $\lambda/10$ with $\lambda$ being the wavelength of the light that is used to examine the surface. It should further be noted that the effect of the roughness depends usually also on the spatial frequency of the surface roughness. In this respect, the dominant spatial frequency of the surface roughness of the carrier will preferably correspond to a wavelength that is of the same order as the roughness, i.e. in a range from 30 to 100 nm. The part of the contact surface that has the defined minimal roughness may particularly be corrugated, i.e. have a periodic or a (quasi-) random structure. The carrier is typically transparent and may optionally be designed such that an input light beam can enter it through an entrance window, be totally internally reflected at the contact surface, and leave it through an exit window.

While it is usually desired to make optical surfaces as smooth as possible to avoid disturbances, the proposed carrier has intentionally a roughness above some threshold value. It turns out that such a high roughness is favorable for a wetting detection, because optical signals are more sensitive to the wetting grade at rough surface regions than at smooth regions.

The invention further relates to another embodiment of a carrier for a microelectronic sensor device of the kind described above, said carrier comprising a contact surface with an investigation region. In this embodiment, the contact surface has a higher roughness in a test region near the investigation region than in the investigation region itself. Said higher roughness may particularly be higher than about 100 nm and/or the roughness inside the investigation region may be lower than 100 nm. Moreover, the test region may optionally encircle the investigation region.

This embodiment of a carrier has the advantage to provide different surface areas which are, with respect to their roughness, optimal for particular purposes (i.e. optical examination in the investigation region and wetting grade detection in the test region).

The invention further relates to a method for making optical examinations in an investigation region at the contact surface of a carrier, said method comprising the following steps:
a) Emitting an input light beam towards the contact surface, wherein said emission is preferably done with a light source of the kind described above.
b) Determining a characteristic parameter of an output light beam that comes from the contact surface, wherein said determination is preferably done with a light detector of the kind described above.
c) Detecting the wetting grade of the investigation region based on the determined characteristic parameter, wherein said detection is preferably done with an evaluation unit of the kind described above.

The method comprises in general form the steps that can be executed with a microelectronic sensor device of the kind described above. Therefore, reference is made to the preceding description for more information on the details, advantages and improvements of that method.

The invention further relates to the use of the microelectronic sensor device and the carrier described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

These and other aspects of the invention will be apparent from and elucidated with reference to the embodiment(s) described hereinafter. These embodiments will be described by way of example with the help of the accompanying drawings in which:

FIG. 1 schematically illustrates the design of a microelectronic sensor device according to the present invention;

Like reference numbers or numbers in the Figures refer to identical or similar components.

Though the present invention will in the following be described with respect to a particular setup (using magnetic particles and frustrated total internal reflection as measurement principle), it is not limited to such an approach and can favorably be used in many different applications and setups.

Figure 1:
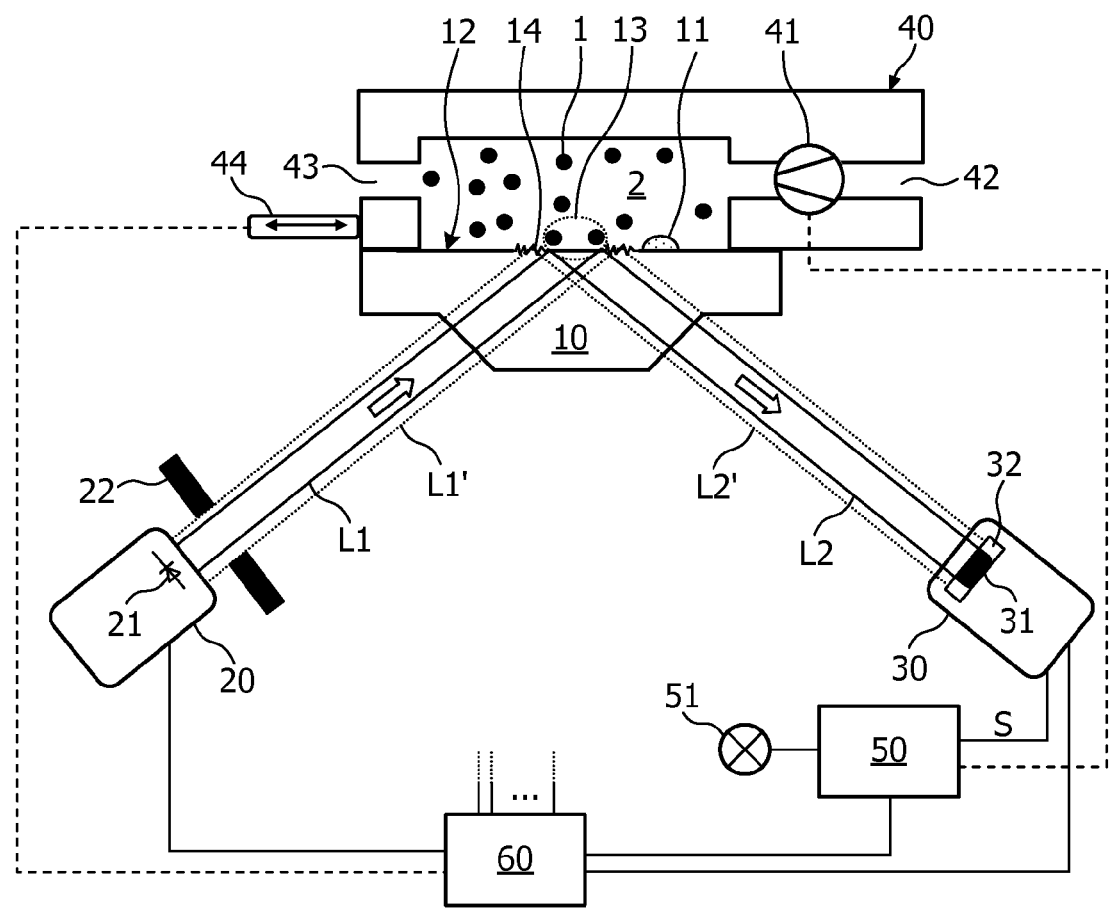

The microelectronic sensor device shown in FIG. 1 comprises a light source 20 with a laser or an LED 21 that generates an "input light beam" L1 which is transmitted through an entrance window into a (disposable) carrier 10 that may for example be made from glass or transparent plastic like polystyrene. The carrier 10 constitutes together with a cover 40 a sample chamber 2 in which a sample fluid with target components to be detected (e.g. small molecules, proteins, metabolites, cells, antibodies, DNA, etc.) can be provided via fluid passages 42 and 43. The sample further comprises magnetic particles 1, for example superparamagnetic beads, wherein these particles 1 are usually bound as labels to the aforementioned target components (for simplicity only the magnetic particles 1 are shown in the Figure). It should be noted that instead of magnetic particles other label particles, for example electrically charged of fluorescent particles, could be used as well.

The interface between the carrier 10 and the sample chamber 2 is formed by a surface called "contact surface" 12. This contact surface 12 may optionally be coated with capture elements, e.g. antibodies, which can specifically bind the target components. The input light beam L1 arrives at the contact surface 12 at an angle larger than the critical angle of total internal reflection (TIR) and is therefore totally internally reflected as an "output light beam" L2. The output light beam L2 leaves the carrier 10 through an exit window and is detected by a light sensitive sensor unit 31 (e.g. a photodiode) in a light detector 30. The light detector 30 thus determines the amount of light of the output light beam L2 (e.g. expressed by the light intensity of this light beam in the whole spectrum or a certain part of the spectrum).

The sensor device optionally comprises a magnetic field generator (not shown), for example an electromagnet with a coil and a core, for controllably generating a magnetic field at the contact surface 12 and in the adjacent space of the sample chamber 2. With the help of this magnetic field, the magnetic particles 1 can be manipulated, i.e. be magnetized and particularly be moved (if magnetic fields with gradients are used). Thus it is for example possible to attract magnetic particles 1 to the contact surface 12 in order to accelerate the binding of the associated target component to said surface.

It is optionally possible to use the detector 30 (or a separate detector) for detecting fluorescence light emitted by fluorescent particles 1 which were stimulated by the evanescent wave of the input light beam L1.

The described microelectronic sensor device applies optical means for the detection of magnetic particles 1 and the target components one is actually interested in. For eliminating or at least minimizing the influence of background (e.g. of the sample fluid, such as saliva, blood, etc.), the detection technique should be surface-specific. As indicated above, this is achieved by using the principle of frustrated total internal reflection. This principle is based on the fact that an evanescent wave propagates (exponentially dropping) into the sample 2 when the incident light beam L1 is totally internally reflected. If this evanescent wave then interacts with another medium like the magnetic particles 1, part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of magnetic beads on or very near (within about 200 nm) to the TIR surface (not in the rest of the sample chamber 2), the reflected intensity will drop accordingly. This intensity drop is a direct measure for the amount of bonded magnetic beads 1, and therefore for the concentration of target molecules. When the mentioned interaction distance of the evanescent wave of about 200 nm is compared with the typical dimensions of anti-bodies, target molecules and magnetic beads, it is clear that the influence of the background will be minimal. Larger wavelengths $\lambda$ will increase the interaction distance, but the influence of the background liquid will still be very small.

The described procedure is independent of applied magnetic fields. This allows real-time optical monitoring of preparation, measurement and washing steps. The monitored signals can also be used to control the measurement or the individual process steps.

For the materials of a typical application, medium A of the carrier 10 can be glass and/or some transparent plastic with a typical refractive index of 1.52. Medium B in the sample chamber 2 will be water-based and have a refractive index close to 1.3. This corresponds to a critical angle $\theta_c$ of 60°. An angle of incidence of 70° is therefore a practical choice to allow fluid media with a somewhat larger refractive index (assuming $n_A$=1.52, $n_B$ is allowed up to a maximum of 1.43). Higher values of $n_B$ would require a larger $n_A$ and/or larger angles of incidence.

Advantages of the described optical read-out combined with magnetic labels for actuation are the following:

Cheap cartridge (i.e. the exchangeable system comprising the carrier 10, cover 40 etc.): The carrier 10 can consist of a relatively simple, injection-molded piece of polymer material.

Large multiplexing possibilities for multi-analyte testing: The contact surface 12 in a disposable cartridge can be optically scanned over a large area. Alternatively, large-area imaging is possible allowing a large detection array. Such an array (located on an optical transparent surface) can be made by e.g. ink jet printing of different binding molecules on the optical surface.

The method also enables high-throughput testing in well-plates by using multiple beams and multiple detectors and multiple actuation magnets (either mechanically moved or electro-magnetically actuated).

Actuation and sensing are orthogonal: Magnetic actuation of the magnetic particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.

The system is really surface sensitive due to the exponentially decreasing evanescent field.

Easy interface: No electrical interconnect between cartridge and reader is necessary. An optical window is the only requirement to probe the cartridge. A contact-less read-out can therefore be performed.

Low-noise read-out is possible.

A problem of the described sensor device is that, for a reliable measurement, the fluid to be tested (saliva, blood, . . . ) needs to be in complete contact with the contact surface 12. During fluid injection, it may however be possible (e.g. due to a manufacturing error or some contamination) that air bubbles 11 get trapped and prevent good "wetting" of the contact surface. In order to prevent a false test result, it is therefore essential to confirm the wetting of the contact surface. Preferably, this wetting detection should be simple, cost-effective, and robust. Moreover, it is desirable to realize it with optical detection, i.e. without a need for electrical contacts, in a way that integrates nicely with the above described optical detection principle and that does not need large modifications to the cartridge or to the read-out configuration.

An additional aspect is that dried buffer chemicals or dried labels are typically present in the biosensor cartridge before a measurement. Redispersion of these chemicals or labels starts when a fluid enters the system and wets the chemicals or labels. At this moment the biochemical reactions of the assay start and the total protocol for performing the assay needs to start at a predefined moment after wetting the chemicals and labels in order to have a reproducible outcome of the assay (as an example: in the case of using magnetic labels the magnetic actuation needs to start at a predefined time).

Additionally, reading out the cartridge consumes power (e.g. for scanning the total investigation region and processing the resulting data digitally). The read-out only needs to start after the biological sample has entered the cartridge. For this reason a method would be beneficial that detects fluid in the cartridge at a low power dissipation mode. When the fluid is detected the reader can switch to a high power dissipation read-out mode.

Figure 2:
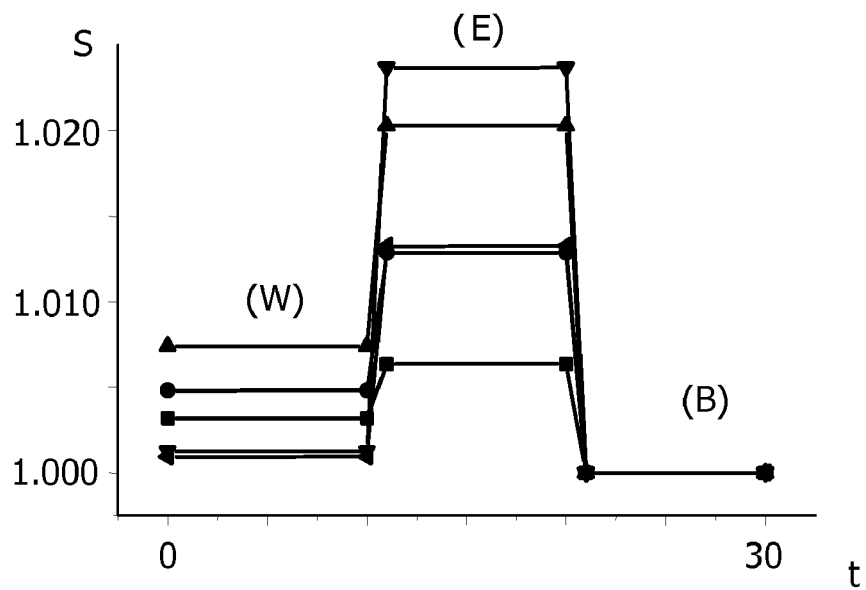
FIG. 2 shows measurement signals for three consecutive filling states of a sample chamber.

The solutions for the above issues that will be described in more detail below are based on the observation that there is a small but significant signal change upon injection of a liquid into an empty sample chamber. This is illustrated in FIG. 2, which shows normalized optical signals S (vertical axis; e.g. light intensities of the output light beam L2) measured over time t (horizontal axis, in arbitrary units) in an experimental setup like that of FIG. 1. The different curves of the diagram correspond to measurements in different sample chambers ("wells") of a well plate and comprise the phases of presence of a wash liquid in the sample chamber (state (W));

removal of the wash liquid and filling of the sample chamber with air to yield the state of an "empty" sample chamber (state (E));

removal of the air and filling of the sample chamber with human blood (yielding state (B)).

The Figure shows that the optical signal S can change by more than 1% upon injection of e.g. water into an empty well, and that the reverse effect occurs when a filled well is emptied. The amplitude of the signal change varies from well to well, but it is reproducible for the same well. It is supposed that this effect is caused by small disturbances and an imperfect smoothness of the contact surface, which leads to some amount of scattering and influences the intensity of the reflected beam. Depending on the refractive index difference with the surrounding medium (liquid or air), the scattering and the total internal reflection will be affected, leading to a slightly different optical signal.

Figure 3:
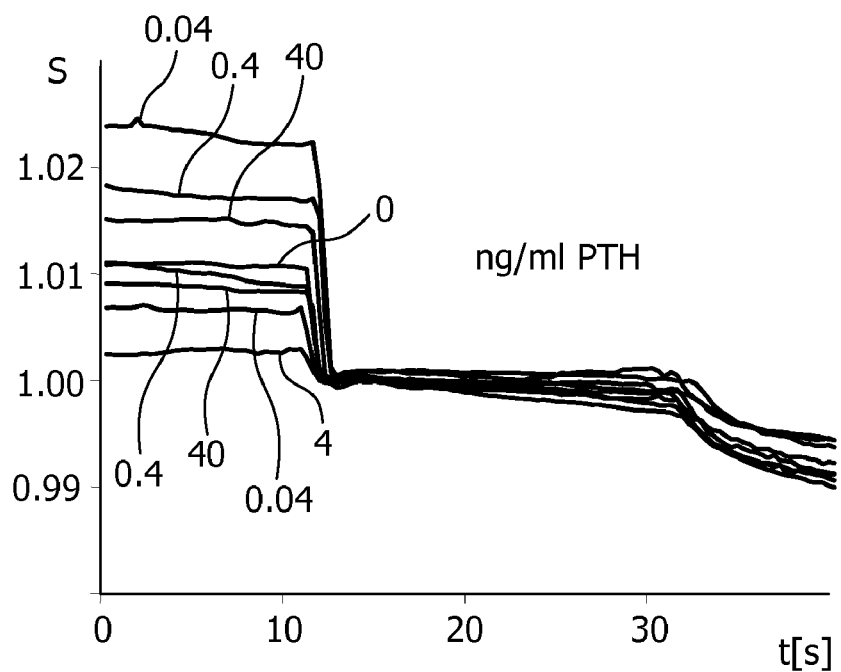
FIG. 3 shows measurement signals for samples with different concentrations of PTH.

FIG. 3 shows in a similar diagram optical measurements that were started with a dry well prepared with PTH (parathyroid hormone) in various concentrations from 0 to 40 ng/ml. At t=12 s, a buffer liquid with 300 nm beads was injected into the well, followed by magnetic attraction (permanent magnet) from t=32 s to t=62 s. Upon injection of the liquid, a signal drop is observed ranging from about 0.25% to more than 2%, independent of concentration. This effect can be used to solve the above problem: An evaluation unit 50 coupled to the light detector 30 (FIG. 1) can process the measurement signals S that are provided to it by the detector 30 and detect a sufficient change (usually a drop) in the signal S upon fluid injection, which indicates wetting. A "sufficient change" may for example be quantified as a change beyond a pre-defined threshold which is chosen significantly larger than the noise level. Any inconsistency (e.g. no change, or change is not detected in all areas) can be used to initiate appropriate measures. Thus the evaluation unit 50 may for example activate a signaling unit 51, e.g. an LED, which indicates the detected wetting grade (or merely an insufficient wetting grade) to the user. The user may then react appropriately, e.g. replace the cartridge or assign a reduced reliability to the measurements. Moreover, the evaluation unit 50 may start an automatic recovery attempt, e.g. by activating an ultrasonic vibrator 44 that acts upon the carrier 10 or its cover 40, or via other means to improve wetting.

The detection of a sufficient or insufficient wetting and/or the quantitative determination of the wetting degree is favorably achieved with the same optical measurement setup that is used for the detection of the target components 1 in the investigation region 13.

To increase the signal change that indicates the wetting of the contact surface 12, the contact surface can intentionally be made non-smooth, i.e. containing small disturbances, or corrugations. As the signal change upon fluid injection is typically about 1%, it can be easily detected, and with a correct normalization directly after injection, measurements are still accurate. Advantages of this approach are that the wetting detection coincides with the bio-detection area, and that no changes or additions to the input light and output light paths are necessary.

For other purposes than wetting detection it is however usually preferable to have a very smooth detection surface that minimizes scattering. In practice, a high-grade optical quality (smoothness of $\lambda/10$ or better) can be achieved also in injection-molded plastic products. Such a smooth surface gives a negligible change in signal upon fluid injection, therefore making it difficult to directly detect wetting.

Figure 4:
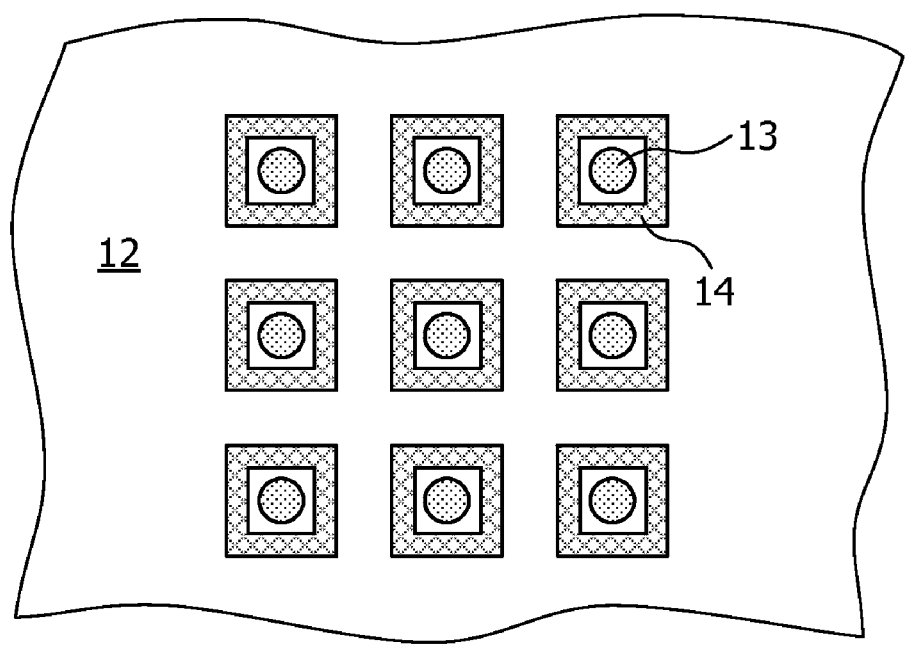
FIG. 4 shows a top view on the contact surface of the carrier shown in FIG. 1.

FIGS. 1 and 4 illustrate a solution to this dilemma: Only small "test regions" 14 close to the investigation region 13 are intentionally made non-smooth or even corrugated in order to promote the signal change effect, while the reminder of the contact surface 12 has a high-grade smoothness. Placing a test region 14 in a strategic location, e.g. around an investigation region 13, and monitoring the signal reflected from this test region 14, allows a very good wetting detection: a signal change beyond a pre-defined threshold (significantly larger than noise level), usually a drop in signal, indicates wetting. Using multiple test regions 14 as shown in FIG. 4 can further improve the reliability.

Separate illumination and/or detection may be used to differentiate the read-out of the test-regions 14 and the investigation regions 13, respectively, and to continuously monitor the wetting of the contact surface. Thus multiplexing possibilities can be applied, for example:

Using a single broad beam L1', L2' and multiple sensor units 31, 32 in the light detector 30 which detect output light form to the test region 14 and the investigation region 13, respectively.

Using multiple laser beams with corresponding sensor units.

Using a single scanning laser with a single sensor unit.

Using pulsed separate, fixed laser beams with a single sensor unit (time-multiplexing).

FIG. 1 illustrates as one solution the changing of the diameter of the input light beam L1, L1'. As shown, this can e.g. be achieved by changing the size of an aperture 22 located in the light path behind the light source 20. The input light beam can then be switched between a small beam L1 that only reaches the investigation region 13 and a broad beam L1' that additionally covers the annular test region 14, said beams leading to a small and a broad output light beam L2, L2', respectively. Other means for adapting the beam width may comprise moving a single (collimator) lens, or applying a voltage to an electro-wetting cell. Using beams L1', L2' with a larger diameter allows to include the test region 14 for wetting detection. After wetting detection, the beam diameter may be reduced to L1, L2 so that only the smooth investigation region 13 is illuminated. This approach allows to use a single, fixed light source 21 (e.g. a laser) and a single sensor unit in the light detector 30 (though FIG. 1 shows two separate sensor units 31, 32 for illustration purposes).

In a further embodiment the sensor device may comprise a sensor array. Data from selected parts of the sensor array (i.e. those parts 32 that contain the wetting information) can be selected and processed until wetting is detected. Then a full-array processing can start in order to measure the assay signals.

FIG. 1 further indicates a "fluid controller" 41 located in an input channel 42 of the cover 40, wherein said controller 41 has a communication link to the evaluation unit 50. The fluid controller 41 can thus provide a triggering signal to the evaluation unit 50 to indicate e.g. that fluid movements in the sample chamber 2 will soon occur, are taking place, or have been accomplished. This allows the evaluation unit to select the right measurement data/times for a correct detection of the wetting grade at the contact surface.

FIG. 1 further shows a higher-level "operation controller" 60 that is coupled to any component of the microelectronic sensor device with which a communication is required, for example to the light source 20, the light detector 30, the evaluation unit 50, the fluidic controller 41, an actuation magnet (not shown), a resistive heating (not shown), and/or the ultrasonic vibrator 44. The operation controller 60 allows to process all the available information and to automatically control as many components of the device as possible to achieve a complete assay control (comprising e.g. magnetic label actuation, (electrical) heating of the sample fluid in the cartridge, control of fluidic pumps and/or fluidic valves, agitation of the magnetic labels in order to improve redispersion (via sonication, di-electrophoresis or any other method), etc.). Thus the number of manual interactions of a user can be reduced to a minimum. This simplifies the handling and, most of all, avoids potential error sources due to the action of a user.

The operation controller 60 can for example use wetting detection to confirm correct insertion of an empty cartridge/carrier 10;

to confirm correct fluid injection and to auto-start the measurement procedure, i.e. magnetic actuation and/or full-speed digital data processing.

These operations are very favorable for example in case of a saliva-based biosensor, for which it is preferable to insert a fresh cartridge into the sensor device and to confirm correct insertion before the saliva sample is introduced. This process order prevents that the beads contained in the cartridge are already dissolving into the liquid long time before the actual assay procedure starts, thus also preventing an unreliable assay measurement. The correct insertion of the cartridge can however automatically be checked using the optical wetting detection:

After cartridge insertion, the optical signal S that is processed by the evaluation unit 50 should indicate that the cartridge is still empty. When the cartridge is not empty, incorrectly inserted or even absent, the signal S will be different from that of a correctly placed, empty cartridge. In case of an error, the cartridge should be replaced. Otherwise the sample can be applied by the user. This can be indicated e.g. by an appropriate (visual and/or audio) signal.

Next, correct sample fluid application is directly checked using the wetting detection. If everything is correct, the measurement procedure can be started automatically. In case of an error, the user can be notified. If no fluid was detected, a reminder signal for fluid or cartridge replacement can for example be given. If a bubble is detected, the cartridge can be vibrated or replaced. At a pre-determined time after a confirmed, correct fluid injection, the measurement procedure is started automatically. This improves reliability and reproducibility of the measurement (as beads start dissolving as soon as the fluid has entered the cartridge). Moreover, user interaction is eliminated, allowing a simpler, more robust user interface and lower cost.

As another measure of automation, the power to the microelectronic sensor device can be switched on/off upon insertion/removal of the cartridge. This can be easily achieved using an internal mechanical switch, which is activated when the cartridge is (fully) inserted. Incorrect insertion is immediately clear (no power, no visual indicator such as a LED). Removing the cartridge switches the power off, thus saving batteries.

While the invention was described above with reference to particular embodiments, various modifications and extensions are possible, for example:

The sensor device can comprise any suitable sensor to detect the presence of magnetic particles on or near to a sensor surface, based on any property of the particles, e.g. it can detect via magnetic methods, optical methods (e.g. imaging, fluorescence, chemiluminescence, absorption, scattering, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on the optical substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device for optical examinations in an investigation region of a carrier, the microelectronic sensor device comprising
    a light source for emitting an input light beam;
    a contact surface for receiving the input light beam and reflecting an output light beam;
    a light detector for determining a characteristic parameter of the output light beam reflected from the contact surface;
    an evaluation unit for when the characteristic parameter indicates wetness, detecting a wetting grade of the investigation region based on the characteristic parameter, the wetting grade indicating an amount of the contact surface by a fluid.

2. The microelectronic sensor device according to claim 1, wherein the characteristic parameter comprises the amount of light of the output light beam.

3. The microelectronic sensor device according to claim 1, wherein the evaluation unit is adapted to determine and compare the characteristic parameters before and after the fluid has been applied to the contact surface.

4. The microelectronic sensor device according to claim 1, wherein the evaluation unit is adapted to process a triggering signal from a fluid controller that controls the application of the fluid to the contact surface.

5. The microelectronic sensor device according to claim 1, wherein the evaluation unit is adapted to determine and compare the characteristic parameters before and after a carrier is placed into the reach of the input light beam.

6. The microelectronic sensor devise according to claim 1, wherein the light source comprises a beam regulator for at least temporarily emitting an input light beam into the surroundings of the investigation region.

7. The microelectronic sensor device according to claim 1, comprising a scanning unit for moving a single light beam, a switching unit for switching between at least two light beams, and/or a collimator unit for changing the width of the input light beam.

8. The microelectronic sensor device according to claim 1, wherein the light detector comprises a plurality of different sensor units associated to different components of the output light beam.

9. The microelectronic sensor device according to claim 1, comprising a signaling unit for indicating the wetting grade, particularly an insufficient wetting, of the investigation region.

10. The microelectronic sensor device according to claim 1, comprising a wetting regulator, particularly an ultrasonic vibrator, for adjusting the wetting of the investigation region.

11. The microelectronic sensor device according to claim 1, comprising an operation controller for controlling the light source and/or the light detector in dependence on the detection result of the evaluation unit.

12. The microelectronic sensor device according to claim 1, wherein the operation controller is adapted to initiate an optical examination in the investigation region after a predetermined wetting grade has been detected.

13. The microelectronic sensor device according to claim 1, comprising a carrier having a contact surface with an investigation region, wherein said contact surface has at least locally a roughness of more than about 100 nm.

14. The microelectronic sensor device according to claim 1, further comprising a carrier having a contact surface with an investigation region, wherein the contact surface has a higher roughness in a test region near the investigation region than in the investigation region.

15. A method for making optical examinations in an investigation region at the contact surface of a carrier, the method comprising acts of:
    emitting an input light beam towards the contact surface;
    determining a characteristic parameter of an output light beam that comes from the contact surface:
    detecting a wetting grade of the investigation region based on the characteristic parameter when the characteristic parameter indicates wetness, the wetting grade indicating an amount of the contact surface contacted by a fluid.

16. The microelectronic sensor device according to claim 1, wherein the device is configured for at least one of molecular diagnostics, biological sample analysis, and chemical sample analysis.

* * * * *